(12) United States Patent
Bailey

(10) Patent No.: US 10,736,977 B2
(45) Date of Patent: Aug. 11, 2020

(54) HIGH INTENSITY NARROW SPECTRUM LIGHT INDICATOR SYSTEMS

(71) Applicant: Hubbell Incorporated, Shelton, CT (US)

(72) Inventor: Christopher Lane Bailey, Greenville, SC (US)

(73) Assignee: Hubbell Incorporated, Shelton, CT (US)

( * ) Notice: Subject to any disclaimer, the term of this patent is extended or adjusted under 35 U.S.C. 154(b) by 0 days.

(21) Appl. No.: 16/278,358

(22) Filed: Feb. 18, 2019

(65) Prior Publication Data

US 2019/0175770 A1    Jun. 13, 2019

Related U.S. Application Data

(63) Continuation of application No. 15/797,706, filed on Oct. 30, 2017, now Pat. No. 10,232,066.

(60) Provisional application No. 62/414,978, filed on Oct. 31, 2016.

(51) Int. Cl.
| | |
|---|---|
| *A61L 2/08* | (2006.01) |
| *G08B 21/18* | (2006.01) |
| *H05B 45/10* | (2020.01) |
| *H05B 45/50* | (2020.01) |

(52) U.S. Cl.
CPC ............ *A61L 2/084* (2013.01); *G08B 21/182* (2013.01); *H05B 45/10* (2020.01); *A61L 2202/14* (2013.01); *H05B 45/50* (2020.01)

(58) Field of Classification Search
CPC .... A61L 2202/14; A61L 2/24; A61L 2202/11; A61L 2202/25; A61L 2209/111; A61L 2209/12; A61L 2/084; A61L 2/10; A61L 9/18; A61L 9/20; A61L 2/0029; A61L 2/0082; A61L 2/0088; A61L 2202/21; A61L 2/0052; A61L 2/12; A61L 5/0625; A61L 9/00
USPC ........................... 340/635, 539.1–19; 422/22
See application file for complete search history.

(56) References Cited

U.S. PATENT DOCUMENTS

| | | |
|---|---|---|
| 3,926,556 A | 12/1975 | Boucher |
| 4,910,942 A | 3/1990 | Dunn et al. |
| 6,251,127 B1 | 6/2001 | Biel |
| 8,398,264 B2 | 3/2013 | Anderson et al. |

(Continued)

FOREIGN PATENT DOCUMENTS

WO    WO2007012875    2/2007

OTHER PUBLICATIONS

Nitzan et al. "ALA induced photodynamic effects on Gram positive and negative bacteria," *Photochem. Photobiol. Sci.*, 2004, 3-18 pages.

(Continued)

*Primary Examiner* — Emily C Terrell
(74) *Attorney, Agent, or Firm* — Michael Best & Friedrich, LLP

(57) ABSTRACT

Indicator systems and methods associated with high intensity narrow spectrum light are provided. In one example embodiment, a lighting system can include one or more high intensity narrow spectrum (HINS) light sources configured to emit HINS light. The system can further include an indicator circuit configured to provide at least one indicator associated with one or more parameters of the HINS light and/or operational performance of the HINS light sources.

19 Claims, 6 Drawing Sheets

(56) References Cited

U.S. PATENT DOCUMENTS

| | | | |
|---|---|---|---|
| 9,039,966 B2 | 5/2015 | Anderson et al. | |
| 9,333,274 B2 | 5/2016 | Peterson et al. | |
| 9,439,989 B2* | 9/2016 | Lalicki | A01K 1/0047 |
| 9,642,356 B2 | 5/2017 | Wood et al. | |
| 9,642,358 B2 | 5/2017 | Cai et al. | |
| 9,700,641 B2 | 7/2017 | Hawkins et al. | |
| 9,927,097 B2 | 3/2018 | Lalicki et al. | |
| 2004/0039242 A1 | 2/2004 | Tolkoff et al. | |
| 2005/0049228 A1 | 3/2005 | Albrecht et al. | |
| 2005/0055070 A1 | 3/2005 | Jones et al. | |
| 2005/0107849 A1 | 5/2005 | Altshuler et al. | |
| 2006/0085052 A1 | 4/2006 | Feuerstein et al. | |
| 2008/0137066 A1 | 6/2008 | Weinstein | |
| 2009/0076115 A1 | 3/2009 | Wharton et al. | |
| 2009/0168396 A1 | 7/2009 | Moriyasu et al. | |
| 2010/0208054 A1 | 8/2010 | Farr | |
| 2010/0246169 A1* | 9/2010 | Anderson | A61L 2/084 362/231 |
| 2010/0277316 A1* | 11/2010 | Schlangen | H05B 45/00 340/540 |
| 2011/0227487 A1 | 9/2011 | Nichol et al. | |
| 2011/0256019 A1 | 10/2011 | Gruen et al. | |
| 2013/0162140 A1* | 6/2013 | Shamoto | G01D 11/28 315/77 |
| 2013/0293156 A1 | 11/2013 | Wells | |
| 2014/0060096 A1 | 3/2014 | Shur | |
| 2015/0002027 A1 | 1/2015 | Huang | |
| 2015/0061510 A1* | 3/2015 | Maxik | H05B 47/10 315/153 |
| 2016/0015840 A1 | 1/2016 | Gordon | |
| 2016/0030609 A1 | 2/2016 | Peterson et al. | |
| 2016/0030610 A1 | 2/2016 | Peterson et al. | |
| 2016/0120410 A1 | 5/2016 | Kim | |
| 2016/0339203 A1 | 11/2016 | Krames et al. | |
| 2016/0361229 A1 | 12/2016 | Na | |
| 2016/0375161 A1 | 12/2016 | Hawkins | |
| 2016/0375162 A1* | 12/2016 | Marry | H01L 33/50 422/22 |
| 2016/0375163 A1 | 12/2016 | Hawkins | |
| 2017/0006685 A1 | 1/2017 | Barron et al. | |
| 2017/0034889 A1 | 2/2017 | Primous et al. | |
| 2017/0080117 A1* | 3/2017 | Gordon | A61L 2/0052 |
| 2017/0101326 A1 | 4/2017 | Zhou | |
| 2017/0101328 A1 | 4/2017 | Smetona et al. | |
| 2018/0121703 A1 | 5/2018 | Jung | |
| 2018/0225498 A1 | 8/2018 | Setlak | |

OTHER PUBLICATIONS

MacLean "An Investigation Into the Light Inactivation of Medically Important Microorganisms," University of Strathclyde, 2006—260 pages.

Nitzan et al., "Endogenous Porphyrin Production in Bacteria by Aminolaevulinic Acid and Subsequent Bacterial Photoeradication," *M. Lasers Med Sci* (Dec. 1999) vol. 14, Issue 4, pp. 269-277.

Ashkenazi et al., "Eradication of Propionibacterium acnes by its endogenic porphyrins after illumination with high intensity blue light," *FEMS Immunology & Medical Microbiology*, vol. 35, Issue 1, Jan. 1, 2003, pp. 17-24.

Ganz et al., "*Helicobacter pylori* in Patients Can Be Killed by Visible Light," *Lasers Surg Med.*, Apr. 2005; 36(4): pp. 260-265.

Møller et al., "How Finsen's light cured lupus vulgaris," *Photodermatol Photoimmunol Photomed* 2005; 21: pp. 118-124.

Kjeldstad, "Photoinactivation of Propionibacterium acnes by Near-Ultraviolet Light," *Zeitschrift für Naturforschung C*, vol. 39, Issue 3-4, 1984, pp. 300-302.

Derosa et al., "Photosensitized singlet oxygen and its applications," *Coordination Chemistry Reviews*, vols. 233-234, Nov. 1, 2002, pp. 351-371.

Elman et al., "The effective treatment of acne vulgaris by a high-intensity, narrow band 405-420 nm light source," *J Cosmetic & Laser Ther* 2003; 5: pp. 111-116.

Konig et al., "Red Light Kills Bacteria via Photodynamic Action," Abstract, *Cellular and molecular biology*, 46(7):1297-303, Dec. 2000—1 page.

Philipp-Dormston et al., "Comparison of Porphyrin and Heme in Various Heterotrophic Bacteria," Abstract, *Enzyme* 16(1):57-64 • Feb. 1973—1 page.

MacLean et al., "405 nm light technology for the inactivation of pathogens and its potential role for environmental disinfection and infection control," *The Journal of Hospital Infection*, Sep. 2014, vol. 88, Issue 1—27 pages.

MacLean et al., "An Innovation: Decontamination by Light—HINS-light Environmental Decontamination System, A new method for pathogen control in the clinical environment," Microsoft Power Point, HINS-light EDS Presentation for Infection Prevention Scotland, The Robertson Trust Laboratory for Electronic Sterilisation Technologies (ROLEST), Oct. 27, 2010—20 pages.

Noimark et al., "Light-activated antimicrobial surfaces with enhanced efficacy induced by a dark-activated mechanism," Chemical Science, Issue 6, Jun. 1, 2014—1 page.

Wallace, John "HINS light kills surface bacteria in hospitals," Laser Focus World, http://www.laserfocusworld.com/articles/2010/11/hins-light-kills-surface.html, accessed on Oct. 30, 2017, PennWell Corporation, Tulsa, OK, Nov. 15, 2010—2 pages.

MacLean et al., Environmental decontamination of a hospital isolation room using high-density narrow-spectrum light, The Hospital Infection Society, Elsevier Ltd., Nov. 2010;76(3)—1 page.

Kenall Mfg. Launches New Bacteiia-killing LED Light for Hospitals, LEDinside, a Business Division of TrendForce Corp., Jun. 29, 2015, accessed on Oct. 30, 2017, http://www.ledinside.com/products/2015/6/kenall_manufacturing_launches_new_uv_led_light_for_hospitals—3 pages.

* cited by examiner

HIGH INTENSITY NARROW SPECTRUM LIGHT INDICATOR SYSTEMS

PRIORITY CLAIM

The present application is a continuation of U.S. application Ser. No. 15/797,706, filed on Oct. 30, 2017, entitled "High Intensity Narrow Spectrum Light Indicator Systems," which claims the benefit of priority of U.S. Provisional Patent Application No. 62/414,978, entitled "High Intensity Narrow Spectrum Light Indicator Systems," filed Oct. 31, 2016, which is incorporated herein by reference for all purposes.

FIELD

The present subject matter relates generally to lighting systems.

BACKGROUND

Lighting systems can be used to provide illumination of spaces and objects for a variety of different applications. In some lighting systems, high intensity narrow spectrum (HINS) light can be used to reduce, suppress, or inactivate bacterial or other microorganisms. For instance, HINS light having a peak wavelength in the range of about 380 nanometers (nm) to about 420 nm (e.g., 405 nm) has been shown to inactivate certain microorganisms, such as certain gram-positive bacteria.

SUMMARY

Aspects and advantages of embodiments of the present disclosure will be set forth in part in the following description, or may be learned from the description, or may be learned through practice of the embodiments.

One example aspect of the present disclosure is directed to a lighting system. The lighting system can include one or more high intensity narrow spectrum (HINS) light sources configured to emit HINS light. The lighting system can further include an indicator circuit. The indicator circuit can be configured to provide an indicator associated with one or more parameters of the HINS light and/or operational performance of the HINS light sources.

Other example aspects of the present disclosure are directed to systems, methods, devices, circuits and apparatus for providing indicators associated with high intensity narrow spectrum light.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussion of embodiments directed to one of ordinary skill in the art are set forth in the specification, which makes reference to the appended figures, in which.

DETAILED DESCRIPTION

Figure 1:
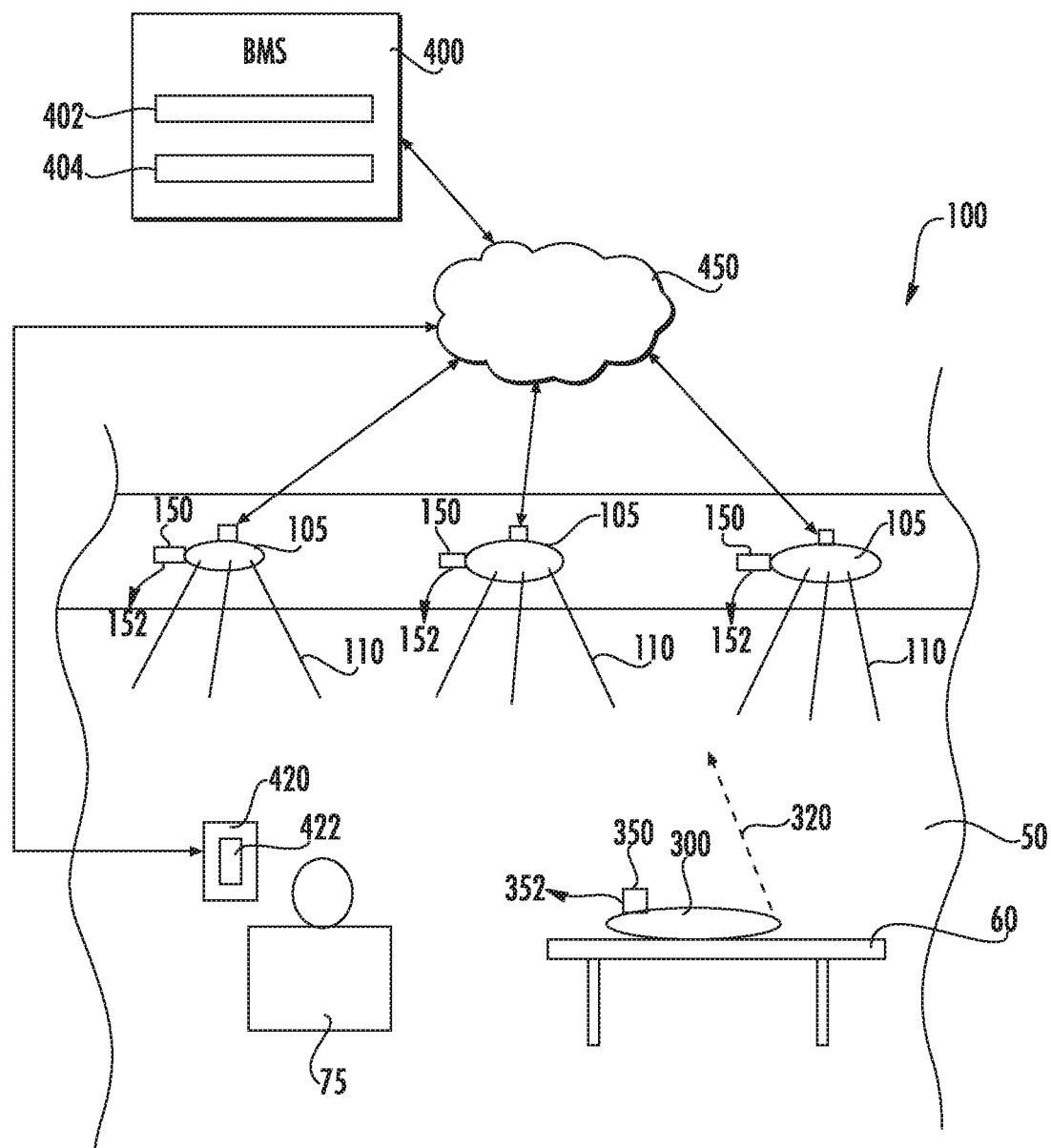
FIG. 1 depicts an overview of an example lighting system according to example embodiments of the present disclosure.

Reference now will be made in detail to embodiments, one or more examples of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations.

Example aspects of the present disclosure are directed to indicators and indicator systems and methods for high intensity narrow spectrum (HINS) lighting systems. A lighting system can be used to illuminate a space and/or surface with HINS light for a variety of purposes, including antimicrobial purposes. The HINS light can include, for instance, light having a peak wavelength in the range of about 380 nanometers (nm) to about 420 nm, such as about 400 nm to about 420 nm, such as about 405 nm. As will be understood by those skilled in the art, using the disclosures provided herein, the HINS light can provide antimicrobial qualities to surfaces upon which the light is emitted. In this manner, the HINS light can reduce, eliminate, suppress and/or inactivate bacterial, fungal, viral, and/or other microorganism contamination on such surfaces.

According to example aspects of the present disclosure, a lighting system can be configured to provide one or more indicators associated with the emission of HINS light. For instance, in some example embodiments, a lighting system can provide one or more visual, audio, and/or data indicators associated with operational characteristics of light source(s) configured to emit HINS light. As an example, a lighting system can provide an indicator when certain local or remote HINS light sources (e.g., LEDs or other light sources configured to emit HINS light) have been operated near or up to intended functional life. In addition and/or in the alternative, an indicator can be provided when HINS light is being emitted by the lighting system, for instance, to dose spaces and/or surfaces with HINS light for antimicrobial purposes (e.g., to reduce, eliminate, or inactive bacterial, fungal, viral, and/or other microorganism contamination on various surfaces and/or in various spaces).

In some example implementations, a lighting system can include an indicator circuit. The indicator circuit can include an optical sensor (e.g., a spectrometer) configured to measure the wavelength and/or other optical properties of light emitted by one or more HINS light sources (e.g., HINS LEDs). The indicator circuit can be configured to provide one or more indicators associated with one or more operational characteristics of the HINS light sources. The one or more indicators can be, for instance, indicative of a wavelength shift by the HINS light sources, signaling that the HINS light sources no longer emit light in the HINS wavelength range (e.g., about 380 nm to about 420 nm, such as about 400 nm to about 420 nm). In these cases, the HINS light sources may be at end of life and need to be replaced. The one or more indicators can be, for instance, a visual notification, audio notification, electronic data notification, etc.

In some embodiments, the one or more indicators can be communicated as one or more data packets or other data transmission over a network (e.g., a wired network, a wireless network, or a combination thereof) to a computing system. The computing system can be any suitable computing device or system, such as one or more laptops, desktops, servers, mobile devices, smartphones, wearable devices (e.g., smartwatches), tablets, or other computing devices. The computing system can process the data packets or other data transmission and provide a notification to users, premise occupants, technicians, and/or others through a suitable user interface and/or output device. The computing system can store the one or more data packets or other data transmission in a suitable memory device so as to retain historical information concerning operation of the lighting system and/or the HINS light sources.

In some embodiments, the computing system can be associated with a building management system or building automated control system. Users of the building management system can interact with the HINS light sources to provide various control functionality. For instance, a user can activate the emission of HINS light via a suitable user interface (e.g., a graphical user interface) provided as part of the building management system. Indicators can be provided to the user regarding operational performance and/or characteristics of the HINS light sources.

Example aspects of the present disclosure are directed to a detection apparatus. The detection apparatus can include a device configured to be placed in a path of light illuminated by one or more HINS light sources. The detection apparatus can be configured to determine whether HINS light is being emitted. The detection apparatus can provide one or more indicators that are indicative of whether HINS light is being emitted by the one or more HINS light sources. The one or more indicators can be, for instance, visual, audio, and/or electronic data indicators.

For instance, in some example implementations, the HINS light detection apparatus can have a circular form factor and can include a spectrometer configured to measure a wavelength of light emitted onto the HINS light detection apparatus. The HINS light detection apparatus can provide one or more indicators based on the light detected at the HINS light detection apparatus. The indicators can be indicative of whether the HINS light detection apparatus is detecting HINS light or whether the HINS is not detecting HINS light. The one or more indicators can be, for instance, on-device indicators, such as visual, audio, or other indicators provided on or from the HINS light detection apparatus. In some embodiments, the one or more indicators can be communicated as electronic data to a remote device (e.g., a remote computing device) over a network. Suitable notifications can then be provided to users, premise occupants, technicians, and/or others from the remote device.

As used herein, a lighting system can include, but is not limited to, one or more of a lighting circuit, light engine, one or more luminaires, one or more lighting fixtures, one or more lighting units, a plurality of lighting devices arranged in an environment, a combination of any of the foregoing, etc. HINS light refers to light having at least one peak wavelength in the range of about 380 nanometers (nm) to about 420 nm, such as about 400 nm to about 420 nm, such as about 405 nm. Non-HINS light refers to light in the visible spectrum, but not in the HINS range of 380 nm to 405 nm. As used herein, the use of the term "about" in conjunction with a numerical value refers to within 5% of the stated numerical value.

FIG. 1 depicts an overview of an example lighting system 100 according to example embodiments of the present disclosure. The lighting system 100 includes a plurality of lighting fixtures 105. Each of the lighting fixtures 105 can be configured to provide light 110 to illuminate a space 50 and/or a surface 60. One or more of the lighting fixtures 105 can include one or more HINS light sources (e.g., HINS LEDs). The HINS light sources can be configured to emit HINS light (e.g., as all or as a part of light 110) into space 50 and/or onto surface 60 for various purposes, such as antimicrobial purposes. Optionally, the lighting fixtures 105 can include one or more non-HINS light sources. The HINS light can be combined with other wavelengths of light emitted by the non-HINS light sources, for instance through electroluminescence or photoluminescence, to create visible white light or other desired effects.

The lighting system 100 can include one or more systems configured to provide indicators associated with operational performance of the HINS light sources in the lighting fixtures 105. Example indicator systems are illustrated in FIG. 1. One or more of these indicators and/or indicator systems can be used either standing alone or in combination with one another without deviating from the scope of the present disclosure. Details concerning the example indicator systems depicted in FIG. 1 will now be set forth.

In example embodiments, the lighting fixtures 105 can each include an output device 150. The output device 150 can be configured to provide an indicator 152 associated with operational performance of the HINS light sources and/or parameters associated with the HINS light. The output device 150 can be a visual output device (e.g., LED, display screen, etc.) that provides a visual or optical signal as an indicator 252. The output device 150 can be an audio device (e.g., audio circuit and speaker) configured to provide an audio signal (e.g., a beep, tone, voice, etc.) as an indicator 252.

As will be discussed in more detail below, the lighting fixtures 105 can provide other indicators associated with operational performance and/or characteristics of the HINS light sources. For instance, indicators can be provided as electronic data over a network 450 to one or more remote computing devices, such as computing device 400 associated with a building management system and/or to user device 420 (e.g., smartphone, tablet, laptop, wearable device, etc.) carried by or otherwise used by user 75. In some embodiments, the lighting fixtures 105 can provide indicators through modulation of light 110 emitted by the lighting fixtures and detected by various image capture devices, such as image capture devices associated with user device 420.

The indicators 252 can be indicative of operational performance or characteristics of the HINS light sources associated with the lighting fixtures 105 and/or can be indicative of parameters associated with the HINS light. For example, in some embodiments, the indicators 252 can indicate that HINS light is no longer being emitted by the HINS light sources (e.g., as a result of wavelength shift by HINS LEDs)

and/or that the HINS light sources are at end of life. In some embodiments, the indicators 252 can indicate that the HINS light is being provided at a level sufficient for dosing purposes (e.g., antimicrobial purposes). In some embodiments, the indicators 252 can be indicative of other operational characteristics, such as operating temperature, intensity, or other operational characteristics of the HINS light sources.

In some embodiments, the lighting fixtures 105 can provide multiple indicators 252 with each indicator indicative of different characteristics or parameters of the HINS light sources and/or HINS light. For instance, a first indicator can be provided when the HINS light source is providing HINS light at a level sufficient for dosing purposes. A second indicator can be provided when the HINS light source is no longer emitting HINS light (e.g., due to wavelength shift). The first indicator can be different from the second indicator. For example, the first indicator can be a first visual signal (e.g., a green illuminated LED) and the second indicator can be a second visual signal (e.g., a red illuminated LED). As another example, the first indicator can be an audio signal and the second indicator can be a visual signal. As yet another example, the first indicator can be a first electronic data type and the second indicator can be a second electronic data type. Various different combinations of indicators can be used to provide information concerning operation and performance of the HINS light sources and/or parameters of the HINS light without deviating from the scope of the present disclosure.

Figure 2:
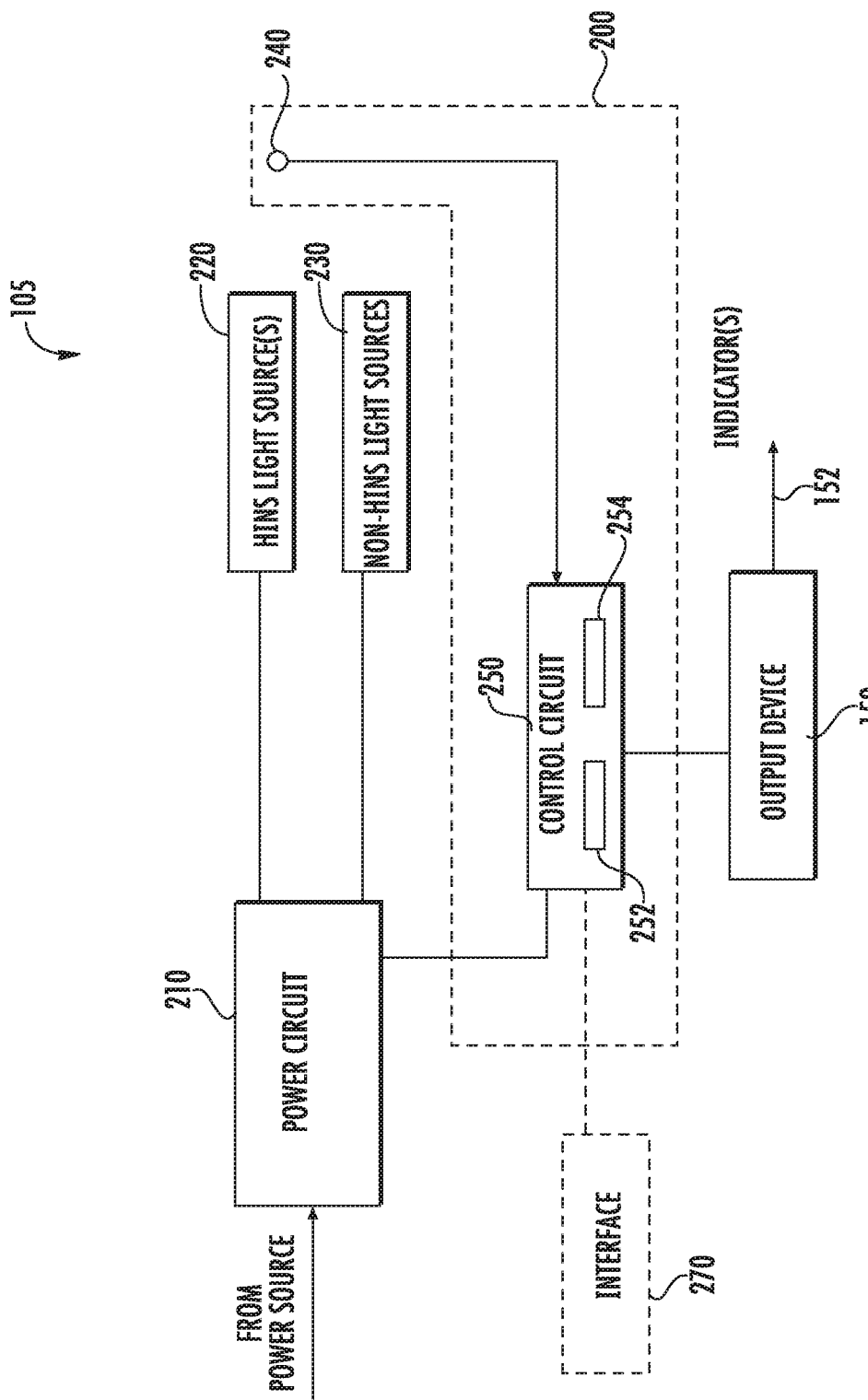
FIG. 2 depicts components of an example lighting fixture according to example embodiments of the present disclosure.

FIG. 2 depicts a block diagram of example components of a lighting fixture 105 configured to provide one or more indicators associated with the emission of HINS light according to example embodiments of the present disclosure. The components shown in FIG. 2 are illustrated as part of the same lighting fixture 105. However, those of ordinary skill in the art, using the disclosures provided herein, will understand that one or more of the components can be distributed across multiple platforms, lighting fixtures, systems, etc.

As shown, the lighting fixture 105 includes a power circuit 210, one or more HINS light sources 220, and an indicator circuit 200. Optionally, the lighting fixture 105 can include one or more non-HINS light sources 230.

The power circuit 210 can receive AC or DC power from a power source and can convert the power to a power suitable for illuminating HINS light sources 220. The power from the power circuit 210 can be provided to the HINS light sources 220 over a suitable channel (e.g., one or more conductors, circuit paths, traces, etc.). Optionally, power can be provided from the power circuit 210 to one or more non-HINS light sources 230 over a suitable channel (e.g., one or more conductors, circuit paths, traces, etc.)

The one or more HINS light sources 220 can be any light sources configured to emit HINS light. As discussed in detail below, in example implementations, the HINS light sources 220 include one or more LED light sources. The present disclosure is discussed with reference to LED light sources for example purposes. Other types of light sources configured to emit HINS light, can be used as HINS light sources 220 without deviating from the scope of the present disclosure.

The one or more non-HINS light sources 230 can be any light sources configured to emit non-HINS light. The one or more non-HINS light sources 230 can be used to emit light to be combined with HINS light to create visible light of a desired color temperature or visual effect. As discussed in detail below, in example implementations, the non-HINS light sources 220 include one or more LED light sources. Other types of light sources configured to emit non-HINS light, can be used as non-HINS light sources 130 without deviating from the scope of the present disclosure.

In embodiments where the lighting fixture 105 is an LED lighting fixture, the power circuit 210 can include an LED driver circuit and the HINS light sources 220 can include and one or more HINS LEDs (e.g., a HINS LED array) configured to emit HINS light. The HINS LEDs can include can include one or more LED devices. The LED devices can emit light as a result of electrons moving through a semiconductor material. The LED devices can be configured to emit HINS light or can include one or more coatings, lenses, materials, etc. that transform light emitted by the LED devices into HINS light.

The LED lighting fixture 105 can optionally include one or more non-HINS LEDs (e.g., a non-HINS LED array) configured to emit non-HINS light. The non-HINS LEDs can include one or more LED devices. The LED devices can be configured to emit non-HINS light of any suitable color and/or color temperature. The HINS LEDs and the non-HINS LEDs can be implemented on the same circuit board or on different circuit boards.

The driver circuit can be, for instance, any suitable driver circuit configured to convert an input power (e.g., an input AC or DC power) to a suitable driver output (e.g. driver current) for powering the HINS LEDs and/or the non-HINS LEDs. In some embodiments, the driver circuit can be a dimmable driver circuit. The driver circuit can be a multi-channel driver circuit configured to power HINS LEDs over a first channel and to power non-HINS LEDs over a second channel. Other suitable arrangements can be used to provide power to the HINS LEDs and/or non-HINS LEDs without deviating from the scope of the present disclosure. For instance, independent driver circuits can be used to power the HINS LEDs and the non-HINS LEDs. As another example, a current splitter circuit can be used to allocate driver current between HINS LEDs and non-HINS LEDs.

In some embodiments, the dimmable driver circuit can include various components, such as switching elements (e.g. transistors) that are controlled to provide a suitable driver output. For instance, in some example embodiments, the driver circuit can include one or more transistors. Gate timing commands can be provided to the one or more transistors to convert the input power to a suitable driver output using pulse width modulation techniques. In some example embodiments, the dimmable driver circuit can be a line dimming driver, such as a phase-cut dimmable driver, Triac dimmer, trailing edge dimmer, or other line dimming driver. The driver output can be adjusted using the line dimming driver by controlling the input power to the dimmable driver circuit.

In some embodiments, the driver circuit can receive a dimming control signal or other control signal used to control the driver output and illumination of the HINS LEDs and/or the non-HINS LEDs. The control signal can be any suitable control signal, such as a 0V to 10V control signal, a DMX control signal, a DALI control signal. The control signal can be communicated over any suitable wired, wireless, or combination of wired and wireless communication media using any suitable protocol.

Example communication technologies can include, for instance, Bluetooth low energy, Bluetooth mesh networking, near-field communication, Thread, TLS (Transport Layer Security), Wi-Fi (e.g., IEEE, 802.11), Wi-Fi Direct (for peer-to-peer communication), Z-Wave, Zigbee, Halow, cellular communication, LTE, low-power wide area networking, VSAT, Ethernet, MoCA (Multimedia over Coax Alliance), PLC (Power-line communication), DLT (digital line transmission), etc. Other suitable wired and/or wireless communication technologies can be used without deviating from the scope of the present disclosure.

As shown, the lighting fixture 105 further includes an indicator circuit 200. The indicator circuit 200 can be configured to monitor operating performance and/or characteristics of the HINS light sources 220 and/or HINS light emitted by the HINS light sources 220 and control the output of indicators 252 by the lighting fixture 105.

The indicator circuit 200 in FIG. 2 includes an optical sensor 240. The optical sensor 240 can include, for instance, a spectrometer, one or more photodiodes, devices for converting light into electrical signals, other sensors, or combination of the foregoing. The optical sensor 240 can be arranged to be in a path of the HINS light emitted by the HINS light sources 220. The optical sensor 240 can generate signals associated with characteristics of the light emitted by the HINS light sources 220, such as signals associated with the wavelength(s) of light emitted by the HINS light sources 220 (e.g., peak wavelengths) and/or signals associated with the intensity of light emitted by the HINS light sources 220.

Other suitable sensors can be used as part of the indicator circuit 200 without deviating from the scope of the present disclosure. For example, the indicator circuit 200 can include temperature sensors or other sensors configured to monitor operational performance and/or characteristics of the HINS light sources 220 and/or light emitted by the HINS light sources 220.

The signals from the optical sensor 240 can be communicated to a control circuit 250. The control circuit 250 can be configured to control the output of indicators based at least in part on signals received from the optical sensor 240 and/or other sensors used as part of the indicator circuit 200.

Figure 5:
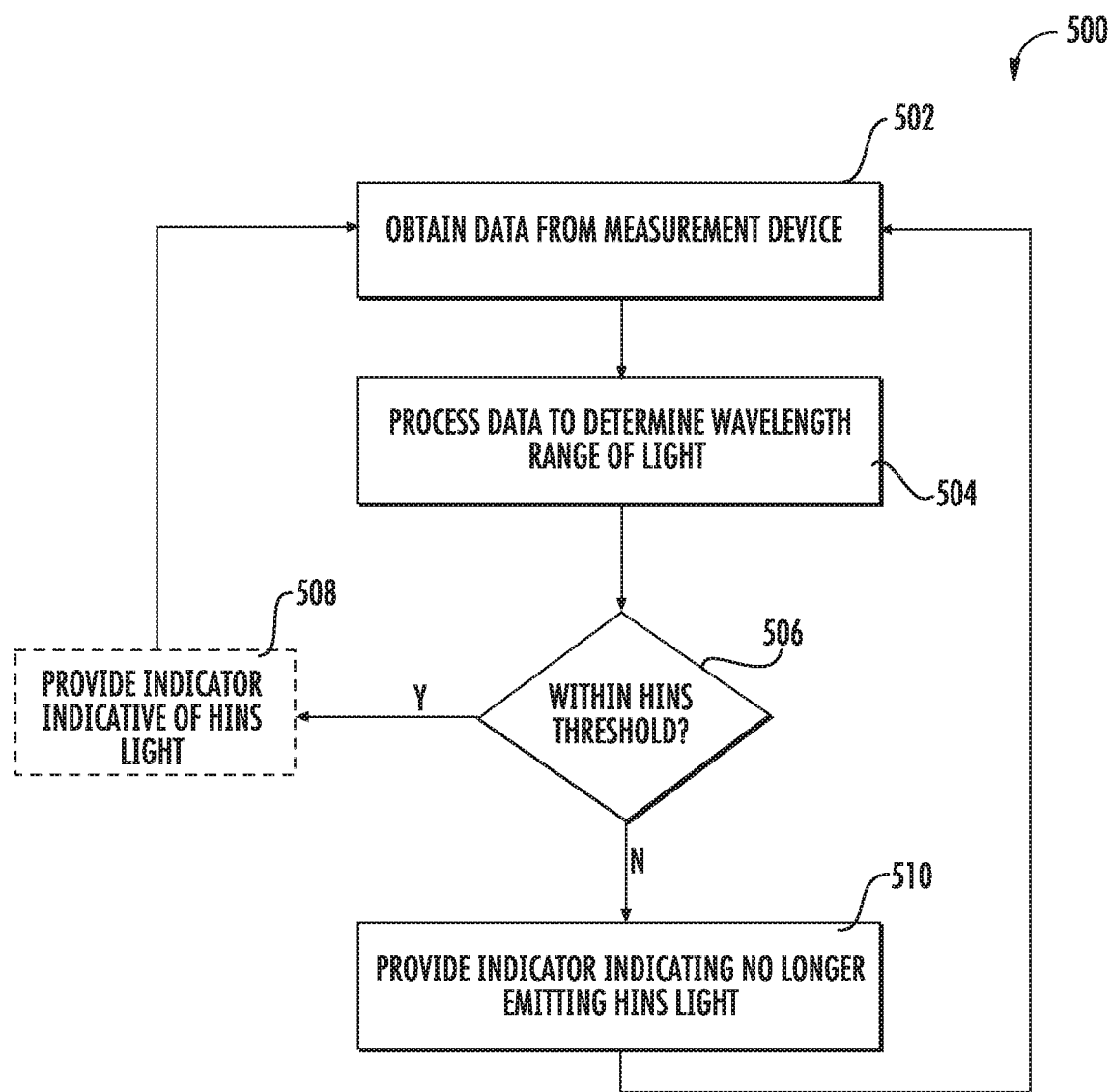
FIG. 5 depicts a flow diagram of an example method according to example embodiments of the present disclosure.
Figure 6:
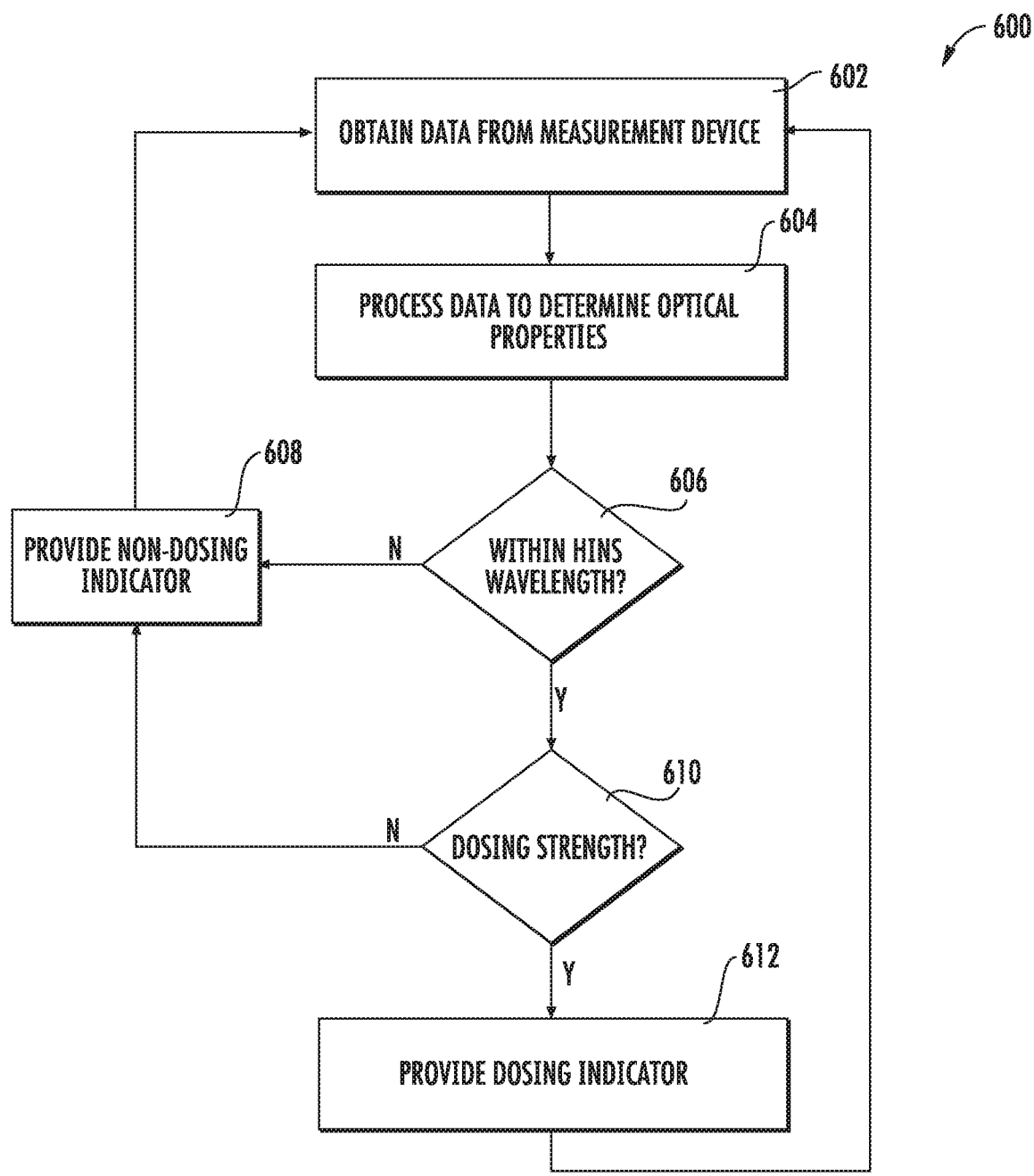
FIG. 6 depicts a flow diagram of an example method according to example embodiments of the present disclosure.

The control circuit 250 and other control circuits or devices disclosed herein can include a microcontroller, microprocessor and one or more memory devices, one or more logic devices, one or more application specific integrated circuits, a control interface, a control system, or other suitable device or circuit that can be provide control functionality according to aspects of the present disclosure, such as the methods illustrated in FIGS. 5 and 6.

In some embodiments, the control circuit 250 can include one or more processors 252 and one or more memory devices 254. The one or more memory devices 254 can store computer-readable instructions that when executed by the one or more processors 252 cause the one or more processors to provide control functionality according to example aspects of the present disclosure. For instance, the one or more memory devices 254 can store computer-readable instructions that when executed by the one or more processors 252 cause the control circuit 250 to control an output device 150 to provide one or more indicators according to example embodiments of the present disclosure.

The output device 150 can be any suitable device configured to provide a visual, audio, electronic data notification, or other suitable indicator 152 according to example embodiments of the present disclosure. For example, the output device 150 can be configured to provide a visual indicator 152 using a display screen, an LED, or other device. The output device 150 can also include one or more speakers or other audio output devices configured to provide an audio indicator 152, such as a beep, tone, sound, voice, speech, or other audio indicator.

The indicator circuit 200 can be implemented on the same circuit board as the power circuit 210 and/or the HINS light sources 220. The indicator circuit 200 can be located remote from the power circuit 210 and/or the HINS LEDs 230. In some embodiments, the control circuit 250 can control the output device 150 over a suitable communication medium, such as a wired or wireless communication medium.

In some embodiments, the control circuit 250 can be configured to provide an indicator as electronic data. The electronic data can be provided in any suitable format and/or protocol. The electronic data can be indicative of operational performance and/or characteristics of the HINS light sources. For example, the electronic data can indicate that HINS light is no longer being emitted by the HINS light sources (e.g., as a result of wavelength shift by HINS LEDs). In some embodiments, the electronic data can indicate that the HINS light is being provided at a level sufficient for dosing purposes (e.g., for antimicrobial purposes). The electronic data can include other information, such as time stamps and other parameters.

As shown in FIG. 2, the control circuit 250 optionally can be coupled to an interface 270 for communicating electronic data and other signals to a remote location. The interface 270 can include one or more components for communicating electronic data to a remote device, for instance, over suitable communications media. For example, the interface 270 can include one or more circuits, terminals, pins, contacts, conductors, transmitters, transceivers, ports, or other components for communicating electronic data to a remote location.

Referring to FIG. 1, in some embodiments, the lighting fixtures 105 can be configured to communicate indicators 152 as electronic data to other lighting fixtures and/or to remote devices, such as remote computing device 400 over a network 450. The network 450 can include, for instance, one or more of a local area network, a home area network, a cellular network, a wide area network, the Internet, or other suitable network. The network 450 can include any combination of wired and/or wireless communication media and can be configured to communicate data using any suitable protocol. The lighting fixtures 105 can communicate data through one or more other lighting fixtures configured as a network of lighting fixtures (e.g., a star network, ring network, mesh network, daisy chain network, communication bus, or other suitable network and/or configuration).

In some embodiments, the lighting fixtures 105 can communicate electronic data as data packets or other data transmission over network 450 to remote computing devices, such as computing device 400 and/or user device 420. Computing device 400 can be any suitable computing device (e.g., laptop, desktop, server, web server, smartphone, tablet, wearable device, etc.). The computing device 400 can include one or more processors 402 and one or more memory devices 404. The processors 402 can be configured to execute computer-readable instructions stored in the one or more memory devices 404 to process and store the electronic data received from the lighting fixtures 105. The electronic data can be stored as data (e.g., in one or more databases) in the one or more memory devices 404.

In some embodiments, the computing device 400 can be associated with a building management system or automated building control system. The building management system or automated building control system can provide one or more user interfaces to allow users, premise occupants, technicians or others to control the lighting system 100 from the computing device 400. For instance, the computing device 400 can be configured to present controls as part of a graphical user interface to allow the user to control the lighting system, such as the emission of HINS light by the lighting fixtures 105. The indicators received as electronic data at the computing device 400 can be presented to the user through a suitable user interface or through an output device (e.g., as visual or audio notifications). The indicators can also be stored in one or more memory devices (e.g., with appropriate time stamps) to allow users to access historical information concerning operational performance and/or characteristics of the HINS light sources, parameters of the HINS light, and/or other components of the lighting system.

As shown in FIG. 1, the indicators 152 in the form of electronic data can be communicated as data packets or other data transmission over network 450 to user device 420. User device 420, in some embodiments, can be a mobile device capable of being carried by a user while in operation (e.g., smartphone, tablet, smartwatch, etc.). The user device 420 can include one or more processors and one or more memory devices for processing the electronic data and/or storing the electronic data in one or more memory devices. The user device 420 can provide the indicators through a suitable output device such as display 422, speaker, vibration, or other output to the user 75. In this way, the user can readily obtain information concerning operational performance and/or characteristic of the HINS light sources from the user device 420 while the user 75 is located in the space 50 and/or near the surface 60.

Indicators as electronic data can be communicated to other remote locations and computing devices (not illustrated in FIG. 1) without deviating from the scope of the present disclosure.

As shown in FIG. 1, example aspects of the present disclosure are directed to a HINS detection apparatus 300. The HINS detection apparatus 300 can be a device that is placed on a surface 60 illuminated by light 110. The HINS detection apparatus 300 can include optical sensors and/or or other measurement devices configured to measure characteristics of the light 110, including HINS light, emitted onto the HINS detection apparatus 300. The HINS detection apparatus 300 can provide one or more indicators 352 (similar to indicators 152) associated with the operational performance and/or characteristics of the HINS light sources or parameters of the HINS light based on measured characteristics of the light 110. The HINS detection apparatus 300 can also provide one or more indicators as electronic data 320 (e.g., through wired or wireless communications media) to be communicated over network 450 to one or more computing devices, such as computing device 400 and/or user device 420.

Figure 3:
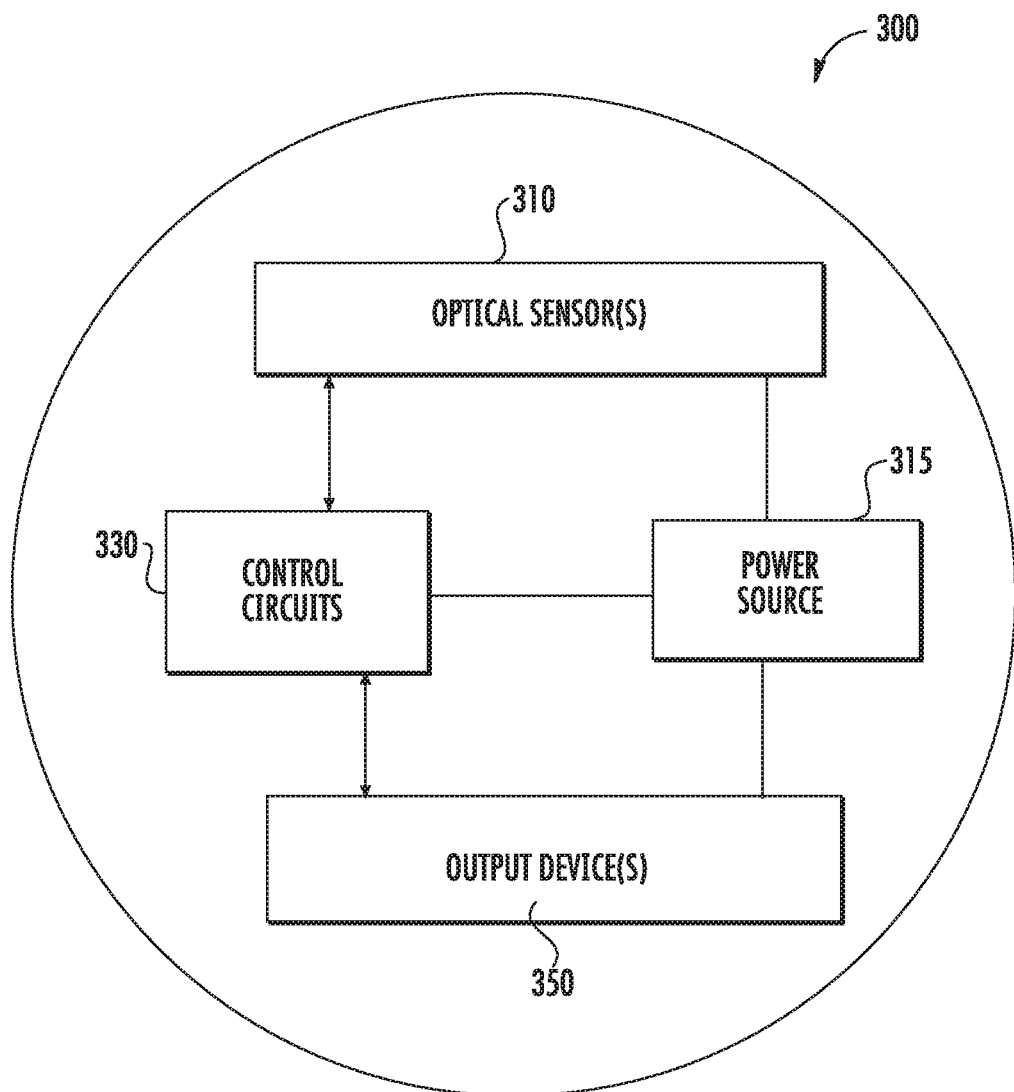
FIG. 3 depicts an example HINS detection apparatus according to example embodiments of the present disclosure.

FIG. 3 depicts a block diagram of an example HINS detection apparatus 300 according to example embodiments of the present disclosure. The apparatus 300 is configured with a circular shape/form factor. However, the HINS detection apparatus 300 can take any suitable shape or form factor without deviating from the scope of the present disclosure.

The HINS detection apparatus 300 includes one or more optical sensors 310, a power source 315, one or more control circuits 330 and one or more output devices 350. The one or more optical sensors 310 can be configured to measure optical properties of light emitted onto the HINS detection apparatus 315 and to generate signals indicative of the optical properties. The optical properties can include, for instance, one or more wavelengths associated with the light and/or an intensity associated with the light. The one or more sensors can include, for instance, a spectrometer, one or more photodiodes, devices for converting light into electrical signals, other sensors, or combination of the foregoing.

The signals indicative of the optical properties of the light can be provided to the control circuit 330. The control circuit 330 can process the signals and control the output device(s) 350 to provide an indicator based at least in part on the signals. For instance, the control circuit 330 can be configured to execute operations described with reference to FIGS. 5 and 6 below.

Referring to FIG. 3, the output device 150 can be located on the HINS detection apparatus 300. The output device can be a visual output device (e.g., LED, display screen, etc.) that provides a visual indicator 252. The output device 150 can be an audio device (e.g., audio circuit and speaker) configured to provide an audio signal (e.g., a beep, tone, voice, etc.) as an indicator 252. In some embodiments, the indicators can be indicative of whether the HINS light detection apparatus is detecting HINS light or whether the HINS is not detecting HINS light.

The power source 315 can be any suitable power source for powering the various components of the HINS detection apparatus 300. In some embodiments, the power source 315 can be a battery power source, solar power source, or other suitable power source so that the HINS detection apparatus 300 does not need to be hard wired to a power source for operation.

Figure 4:
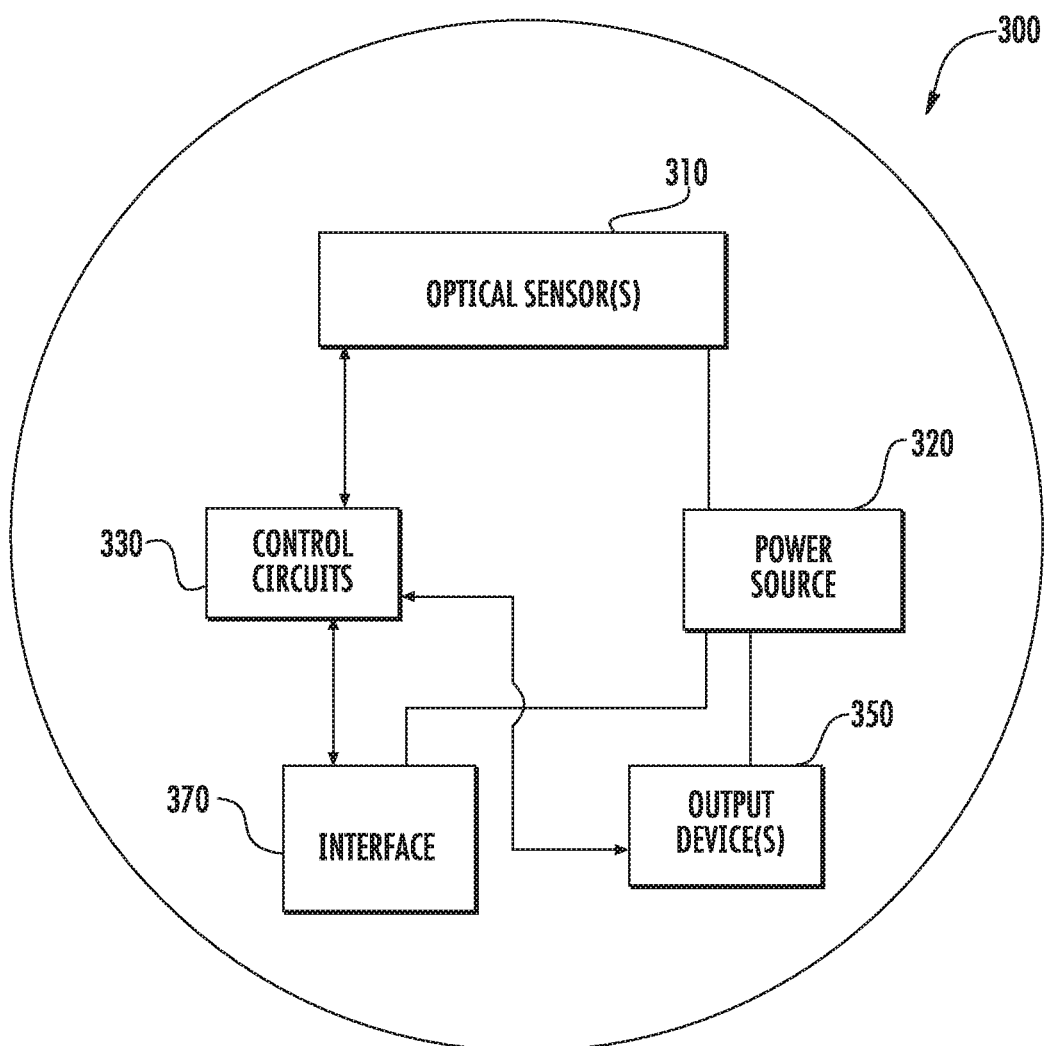
FIG. 4 depicts an example HINS detection apparatus according to example embodiments of the present disclosure.

FIG. 4 depicts a HINS detection apparatus 300 according to example embodiments of the present disclosure. The HINS detection apparatus 300 of FIG. 3 is substantially similar to that of FIG. 4, except that the HINS detection apparatus 300 of FIG. 4 additionally includes an interface 370 for communicating indicators (e.g., as electronic data) to remote devices, for instance, over a network. The interface 370 can include one or more components for communicating electronic data to a remote device, for instance, over suitable communications media. For example, the interface 370 can include one or more circuits, terminals, pins, contacts, conductors, transmitters, transceivers, ports, or other components for communicating electronic data to a remote location.

Example communication technologies can include, for instance, Bluetooth low energy, Bluetooth mesh networking, near-field communication, Thread, TLS (Transport Layer Security), Wi-Fi (e.g., IEEE, 802.11), Wi-Fi Direct (for peer-to-peer communication), Z-Wave, Zigbee, Halow, cellular communication, LTE, low-power wide area networking, VSAT, Ethernet, MoCA (Multimedia over Coax Alliance), PLC (Power-line communication), DLT (digital line transmission), etc. Other suitable wired and/or wireless communication technologies can be used without deviating from the scope of the present disclosure.

Other indicators and devices can be used to provide notifications associated with operational performance and/or characteristics of HINS light sources or parameters associated with HINS light without deviating from the scope of the present disclosure. For instance, a substrate (e.g., a paper like substrate) can be placed in the path of HINS light. The substrate can be configured to change color when exposed to HINS light to provide an indicator of whether a surface is being exposed to HINS light.

FIG. 5 depicts a flow diagram of one example method (500) according to example embodiments of the present disclosure. The method (500) can be implemented by, for instance, a control circuit, such as the control circuit 250 of FIG. 2 or the control circuit 330 of FIGS. 3 and 4. FIG. 5 depicts steps performed in a particular order for purposes of illustration and discussion. Those of ordinary skill in the art, using the disclosures provided herein, will understand that various steps of any of the methods disclosed herein can be omitted, rearranged, expanded, adapted, and/or modified in various ways without deviating from the scope of the present disclosure.

At (502), the method can include obtaining data from a measurement device, such as an optical sensor. The data can be indicative of optical characteristics of light emitted onto the optical sensor. For instance, signals associated with a wavelength of light generated by an optical sensor (e.g. spectrometer) can be accessed by a control circuit. At (504), the data from the measurement device can be processed to determine a wavelength or multiple wavelengths associated with the light emitted on the measurement device.

At (506), the method can include comparing the wavelengths with a predefined range of HINS wavelengths associated with HINS light. The predefined range of HINS wavelengths can be, for instance, 380 nm to 420 nm, 400 nm to 420 nm, 405 nm, or any other wavelength or range of wavelengths between 380 nm and 420 nm.

When the light emitted onto the measurement device includes light having a wavelength that is within the range of HINS wavelengths, the method can optionally include at (508) providing an indicator signaling that HINS light is being emitted. In the event (508) is not performed when the light emitted onto the measurement device includes light having a wavelength that is within the range of HINS wavelengths, the method can continue obtaining data from the measurement device as shown in FIG. 5.

When the light emitted onto the measurement device does not include light having a wavelength that is within the range of HINS wavelengths, the method can include at (510) providing an indicator signaling that HINS light is no longer being emitted. In this way, the method (500) can be used to notify a user, premise occupant, or technician that corrective action needs to take place to make sure HINS light is being emitted into a space or onto a surface.

FIG. 6 depicts a flow diagram of another example method (600) according to example embodiments of the present disclosure. The method (600) can be implemented by, for instance, a control circuit, such as the control circuit 250 of FIG. 2 or the control circuit 330 of FIGS. 3 and 4. FIG. 6 depicts steps performed in a particular order for purposes of illustration and discussion. Those of ordinary skill in the art, using the disclosures provided herein, will understand that various steps of any of the methods disclosed herein can be omitted, rearranged, expanded, adapted, and/or modified in various ways without deviating from the scope of the present disclosure.

At (602), the method can include obtaining data from a measurement device, such as an optical sensor. The data can be indicative of optical characteristics of light emitted onto the optical sensor. For instance, signals associated with a wavelength of light generated by an optical sensor (e.g. spectrometer) can be accessed by a control circuit. At (604), the data from the measurement device can be processed to determine optical properties, such as wavelength and intensity, associated with the light emitted on the optical sensor.

At (606), the method can include comparing the wavelengths with a predefined range of HINS wavelengths associated with HINS light. The predefined range of HINS wavelengths can be, for instance, 380 nm to 420 nm, 400 nm to 420 nm, 405 nm, or any other wavelength or range of wavelengths between 380 nm and 420 nm. When the light emitted onto the optical sensor includes light having a wavelength that is not within the range of HINS wavelengths, the method can include at (608) providing an indicator signaling that dosing with HINS light (e.g., for antimicrobial purposes) is not occurring.

When the light emitted onto the measurement device does include light having a wavelength that is within the range of HINS wavelengths, the method can continue to (610) where intensity is compared to a threshold dosing strength of HINS light. The threshold dosing strength can be defined to be any suitable value, such as a value sufficient to provide for antimicrobial effects. When the light emitted onto the measurement device has an intensity that does not meet the threshold, the method include at (608) providing an indicator signaling that dosing with HINS light is not occurring. When the light emitted onto the measurement device does meet the threshold, the method can include at (612) providing an indicator signaling that dosing with HINS light is occurring.

FIGS. 5 and 6 provide example methods of providing indicators associated with HINS light. Other example methods of providing indicators associated with HINS light can be performed without deviating from the scope of the present disclosure.

While the present subject matter has been described in detail with respect to specific example embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A lighting system, comprising:
 a high intensity narrow spectrum (HINS) light source configured to emit HINS light;
 a non-HINS light source configured to emit non-HINS light; and
 an indicator circuit,
 wherein the HINS light source and the non-HINS light source are arranged such that when the HINS light source emits HINS light and the non-HINS light source emits non-HINS light, the HINS light and the non-HINS light combine to create visible light,
 wherein when the HINS light source is emitting HINS light, the indicator circuit is configured to provide a first indicator, and
 wherein when the HINS light source is emitting non-HINS light, the indicator circuit is configured to provide a second indicator that is different than the first indicator.

2. The lighting system of claim 1, wherein when a wavelength of light emitted from the HINS light source is within a threshold of HINS light, the indicator circuit is configured to provide the first indicator.

3. The lighting system of claim 1, wherein when a wavelength of light emitted from the HINS light source is not within a threshold of HINS light, the indicator circuit is configured to provide the second indicator.

4. The lighting system of claim 1, wherein the first indicator is a dosing indicator indicative of the HINS light source dosing a space or surface with HINS light.

5. The lighting system of claim 1, wherein the second indicator is a non-dosing indicator indicative of the HINS light source dosing a space or surface with non-HINS light.

6. The lighting system of claim 1, wherein a color temperature of the visible light corresponds to a color temperature associated with white light.

7. The lighting system of claim 1, wherein the indicator circuit further comprises a control circuit configured to control an output device on a lighting fixture of the lighting system to provide the first indicator and the second indicator.

8. The lighting system of claim 1, wherein the first indicator and the second indicator comprises a visual indicator, an audio indicator, or modulated light output by the lighting system.

9. The lighting system of claim 1, wherein the HINS light has a wavelength of about 405 nm.

10. A method of providing an indicator associated with high intensity narrow spectrum (HINS) light, the method comprising:
  providing a combined light output comprising light emitted from a HINS light source and light emitted from a non-HINS light source;
  obtaining data associated with the light emitted from the HINS light source;
  determining whether the light emitted from the HINS light source is HINS light or non-HINS light based at least in part on the data;
  responsive to determining the light emitted from the HINS light source is HINS light, providing a first indicator; and
  responsive to determining the light emitted from the HINS light source is non-HINS light, providing a second indicator that is different than the first indicator.

11. The method of claim 10, wherein the first indicator is a dosing indicator indicative of the HINS light source dosing a space or surface with HINS light.

12. The method of claim 10, wherein the data comprises a wavelength of the light emitted from the HINS light source.

13. The method of claim 12, wherein determining whether the light emitted from the HINS light source is HINS light or non-HINS light comprises determining whether the wavelength is within a threshold of HINS light.

14. The method of claim 10, wherein the second indicator is a non-dosing indicator indicative of the HINS light source dosing a space or surface with non-HINS light.

15. The lighting system of claim 10, wherein the first indicator and the second indicator comprise at least one of a visual indicator or an audio indicator.

16. The lighting system of claim 10, wherein providing the indicator comprises providing the indicator via an output device of a lighting fixture.

17. A high intensity narrow spectrum (HINS) detection apparatus operable to be placed on a surface illuminated by light emitted from a HINS light source of a lighting system, the HINS detection apparatus comprising:
  an optical sensor configured to detect optical properties of the light when the HINS detection apparatus is placed on the surface such that the optical sensor is arranged in a path of the light emitted from the HINS light source, the optical sensor further configured to generate one or more signals indicative of the optical properties; and
  a control circuit configured to:
    process the one or more signals indicative of the optical properties to determine whether the HINS light source is emitting HINS light or non-HINS light;
    responsive to determining the HINS light source is emitting HINS light, control an output device to provide a first indicator; and
    responsive to determining the HINS light source is emitting non-HINS light, control the output device to provide a second indicator that is different than the first indicator.

18. The lighting system of claim 1, wherein:
the first indicator comprises light having a first color temperature; and
the second indicator comprises light having a second color temperature that is different than the first color temperature.

19. The lighting system of claim 1, wherein:
the first indicator comprises a visual indicator; and
the second indicator comprises an audible indicator.

* * * * *